(12) United States Patent
Ecker

(10) Patent No.: US 8,900,255 B2
(45) Date of Patent: Dec. 2, 2014

(54) ANASTOMOTIC TISSUE CONNECTION DEVICE

(76) Inventor: Karl-Wilhelm Ecker, Waren (DE)

( * ) Notice: Subject to any disclaimer, the term of this patent is extended or adjusted under 35 U.S.C. 154(b) by 604 days.

(21) Appl. No.: 12/682,328

(22) PCT Filed: Oct. 10, 2008

(86) PCT No.: PCT/EP2008/063592
§ 371 (c)(1),
(2), (4) Date: Jun. 11, 2010

(87) PCT Pub. No.: WO2009/047320
PCT Pub. Date: Apr. 16, 2009

(65) Prior Publication Data
US 2010/0262170 A1 Oct. 14, 2010

Related U.S. Application Data

(60) Provisional application No. 60/979,086, filed on Oct. 11, 2007.

(30) Foreign Application Priority Data

Oct. 11, 2007 (DE) .................. 10 2007 049 629

(51) Int. Cl.
*A61B 17/04* (2006.01)
*A61B 17/11* (2006.01)
*A61B 17/115* (2006.01)

(52) U.S. Cl.
CPC ....... *A61B 17/115* (2013.01); *A61B 2017/1142* (2013.01)
USPC ...... 606/142; 606/219; 227/175.1; 227/176.1

(58) Field of Classification Search
USPC ......... 606/139, 142, 143, 148–150, 153, 154, 606/157, 158, 219, 220; 227/175.1, 227/176.1–181.1, 19, 901, 902
See application file for complete search history.

(56) References Cited

U.S. PATENT DOCUMENTS

| 4,603,693 A | * | 8/1986 | Conta et al. ................ 227/179.1 |
| 5,193,731 A | * | 3/1993 | Aranyi ............................ 227/19 |
| 6,030,370 A | * | 2/2000 | Kupka et al. ................... 604/264 |
| 6,050,472 A | * | 4/2000 | Shibata ....................... 227/175.2 |

(Continued)

FOREIGN PATENT DOCUMENTS

| DE | 3152428 C2 | 8/1986 |
| DE | 69009935 T2 | 12/1994 |
| DE | 69218268 T2 | 7/1997 |
| EP | 0427949 A1 | 5/1991 |

(Continued)

*Primary Examiner* — Melanie Tyson
*Assistant Examiner* — Todd J Scherbel
(74) *Attorney, Agent, or Firm* — Norris McLaughlin & Marcus, P.A.

(57) ABSTRACT

An anastomotic tissue connection device has a head side end and a handle side end, with a head part arranged at the head side end. The head part has a reception means for receiving at least one connection member and which is, furthermore, provided with a counter-pressure plate being firmly arranged at a counter-pressure plate holding device and facing the head part. The head part and the counter-pressure plate holding device are relatively movable towards each other. For the support of the counter-pressure plate, the counter-pressure plate holding device forms at least one column so that a space directly behind the counter-pressure plate is freely accessible radially to a circumference of the counter-pressure plate.

18 Claims, 6 Drawing Sheets

(56) References Cited

U.S. PATENT DOCUMENTS

| | | | |
|---|---|---|---|
| 6,083,241 A * | 7/2000 | Longo et al. | 606/219 |
| 6,117,148 A | 9/2000 | Ravo | |
| 6,126,058 A * | 10/2000 | Adams et al. | 227/180.1 |
| 6,740,098 B2 * | 5/2004 | Abrams et al. | 606/148 |
| 7,118,528 B1 * | 10/2006 | Piskun | 600/105 |
| 2010/0019016 A1 * | 1/2010 | Edoga et al. | 227/179.1 |

FOREIGN PATENT DOCUMENTS

| | | |
|---|---|---|
| EP | 0495673 A1 | 7/1992 |
| EP | 1239781 A1 | 9/2002 |
| EP | 1775449 A1 | 4/2007 |
| WO | 03/090631 A1 | 11/2003 |
| WO | 2004/058080 A2 | 7/2004 |
| WO | 2005/023092 A2 | 3/2005 |

* cited by examiner

ANASTOMOTIC TISSUE CONNECTION DEVICE

This application is a 371 application of PCT/EP2008/063592 filed Oct. 11, 2008, which claims priority to the German application 10 2007 0490629.1 filed Oct. 11, 2007 and U.S. provisional application 60/979,086 filed Oct. 11, 2007.

The invention relates to an anastomotic tissue connection device in the form of a mechanical circular suture clip device for making irreversible intestinal connections (anastomoses). It has a head side end and a handle side end, with a head part arranged at the head side end comprising a reception means for receiving at least one connection member for the connection of the tissue. Furthermore, it is provided with a counter-pressure plate being firmly arranged at a counter-pressure plate holding device and facing the head part for retention during the introduction of the connection member into the tissue that is to be connected, with the head part and the counter-pressure plate holding device being relatively movable towards each other.

Surgical interventions at the intestines can be made substantially easier by means of mechanical suture devices, sometimes, however, they are only made possible is through them. If one simply looks at the intestines as a tube, one can exclusively reunite (anastomosis formation) intestine ends surgically prepared in a different way by means of conventional circular suture clip devices. In some indications, the intussusception of the intestine into the suture device is required. Indications for this are: the internal prolapse of the rectum as a spontaneous intussusception, the anus and rectum prolapse as well as the prolapsing haemorrhoidal condition. Pathological changes, such as polypi and early stages of cancer may, however, also be removed in this way by creating an artificial intussusception and using the same for the resection. If one leaves out during the process of suturing the working step of the resection and if one applies only the circular clip suture row, a so-called nipple valve is created from the intussusception. The volume flow within the intestines is thus influenced in the desired manner by unidirectional transmissibility and retrograde pressure competence. Indications for this are the formation of nipple valves in the continent ileostomy or continent urostomy (Kock Pouch) and the formation of nipple valve anastomoses for the prevention of the relapse of the neo-terminal ileum following ileocolic resection in M. Crohn.

For carrying out the above-mentioned operations, a circular suture clip device is usually used which, depending upon the respective case, is equipped with or without a cutting means for tissue separation. Such a suture clip device is operated manually and can be monitored with the human eye due to the fact that the site of operation is not far from the intestinal opening. For preparing the tissue that is to be removed and/or connected, sutures are advantageously laid within the intestine and/or within its mucous membrane, with the threads of which the tissue of the intestines and/or of the mucous membrane can be positioned in such a manner that a precise and effective cutting and/or connection operation can be carried out by means of the circular suture clip device. For keeping the end of the intestine open for the easy introduction and positioning of the suture clip device, a ring speculum which is introduced into the end of the intestine is usually used. This makes it possible for the surgeon to get a view of the site of the operation in the intestine through the ring speculum as well as to guide and to position the preparatory sutures next to the suture clip device. To this date, it is not possible to carry out the mentioned operations in one single working step. With the exception of haemorrhoidal surgery linear, convexly bent or circular is suture clip devices must always be used in several successive working steps. The reason for this is that circular suture clip devices of the state of the art are always provided with a housing into which the invaginated intestine must be pulled. Owing to the fact that the capacity of the same is limited and that this capacity cannot be enlarged, intussusceptions can only be removed in fractions or recourse must be made to convexly bent linear suture clip devices (internal prolapse) or to linear suture clip devices (nipple valve). This does, however, considerably increase the risk of complications during surgery.

From DE 692 18 268 T2 a circular suture clip device is known which is provided with a tissue-piercing plate with teeth and comprises a receiving plate, the receiving plate being configured so that it receives and engages the teeth of the tissue-piercing plate. The two plates are breakable within the circumference. Here, the teeth are the members which connect the two plates with each other, and they are arranged at the head part of the suture clip device. The engagement means for the teeth in form of the receiving plate is arranged at the handle part. After surgery, the two rings remain in the tissue. This brings about a reduction of the cross section in the intestine. The preparations for the connection of the two halves of the intestines are made complicated since due to the small area that is available within the intestines the manipulation of the tissue that is to be connected with the suture clip device having been introduced is difficult.

A similar device is shown by DE 690 09 935 T2 where also in a device for the suturing of anastomoses in surgical interventions clips that are housed in a clip magazine in a head part co-operate with an anvil that is arranged at a guiding part. Drive means which cause a relative movement of the head part to the handle part thus facilitating a clamping of intestinal tissue are arranged at the end of a tubular section. This tubular section of the suture clip device facilitates the use of the device in areas of the intestines which are comparatively far away from an end of the intestine. Due to the great distance of the site of operation from the end of the intestine, it is thus not possible to lay a suture within the intestines in preparation of the surgical intervention and to bring by means of adjusting the suture thread the intestinal tissue in a position that is favourable for the intervention.

An object of the invention is to provide a suture clip device that is cost-efficient, that works efficiently and that makes the surgical intervention easier for the surgeon by means of which invaginations, such as, for instance, prolapses can be removed, the pexis of haemorrhoids by means of the resection of suprahaemorrhoidal mucosal collars is possible, the resection of other pathological changes, such as adenomas and early stages of cancer can be made via intestinal invagination and by means of which nipple valves and nipple valve anastomoses can be stabilised.

This object is accomplished by the invention by means of the anastomotic tissue connection device as claimed in Claim 1. Advantageous configurations of the tissue connection device are described in the dependent claims which follow Claim 1.

An anastomotic tissue connection device in the form of a mechanical circular suture clip device is provided which has a head side end and a handle side end with a head part arranged at the head side end comprising a reception means for receiving at least one connection member for the connection of the tissue. Furthermore, the tissue connection device is provided with a counter-pressure plate being firmly arranged at a counter-pressure plate holding device and facing the head part for retention during the introduction of the connection member into the tissue that is to be connected, with the head part and the counter-pressure plate holding device being relatively movable towards each other. For the support of the counter-pressure plate, the counter-pressure plate holding device forms at least one column which is positioned and dimensioned in such a manner that the space directly behind the counter-pressure plate is freely accessible radially to the circumference of the counter-pressure plate, with the exception of the space which is occupied by the column. Owing to the essentially cylindrical shape of the housing of the tissue connection device, the counter-pressure plate constitutes a circular area. This circular area is held in the to counter-pressure plate holding device preferably by means of two to four columns. This specific arrangement of the counter-pressure plate makes it possible that the space behind the counter-pressure plate, i.e. the space between the counter-pressure plate and the handle side end of the tissue connection device is easily accessible for manual operations and also optically since radially to the circumference is of the counter-pressure plate and radially to the circumference of the body of the counter-pressure plate holding device which is formed by the columns around the space behind the counter-pressure plate the stitching as well as the arrangement of the tissue that is to be removed or connected is made easier for the surgeon. This is ensured in particular by the arrangement of the clip magazine in the head part and by the arrangement of the counter-pressure plate at the side opposite the head part on the handle-side counter-pressure plate holding device. The invention is not limited to the use of one column only, while when only one column is used, only very little space is occupied by the column behind the counter-pressure plate providing thereby all the more space for the positioning and fixing of tissue as well as for the positioning of the suture. A bending of the column which supports the counter-pressure plate and thus a displacement of the counter-pressure plate can be counteracted by an appropriate material of the column or by its constructive design. In the advantageous arrangement of two to four columns for the support of the counter-pressure plate, the columns form some kind of cage into which the tissue that is to be treated and/or that is to be cut off can be properly positioned. The columns can have a correspondingly thin design so that a very good accessibility to the space behind the counter-pressure plate is still given. In this case, the columns are advantageously 6 cm to 8 cm long. The invention is, however, not limited to these length dimensions, and it may well be of advantage to use connection devices with shorter or longer columns, depending upon the site of operation and/or upon the task to be performed by the surgeon. Preferably, the columns are attached to the counter-pressure plate at its outer circumference in order to maximise the space between the columns thus offering the opportunity to pull a maximum amount of tissue into the space behind the counter-pressure plate between the columns. Owing to the inventive configuration of the tissue connection device as a suture clip device wherein the clips and the cutting means are arranged in the head part and the space behind the counter-pressure plate is available for the reception of tissue, much more tissue, for instance of a prolapse can be removed by means of the inventive tissue connection device by one actuation only of the connection device since much more space for pulling in and positioning of the tissue is available behind the counter-pressure plate than with conventional suture clip devices. For the removal of such a great amount of tissue as is possible with the inventive device, several cuts had to be performed when compared with the embodiments known from the state of the art in order to be able to remove as much tissue by means of a total of individual cuts as can be accomplished with one single cut only according to the present invention. This means that with the conventional use of the suture clip device as one-way products, at least two suture clip devices had to be used for each prolapse removal while this can be accomplished with one device only and/or with one actuation only of the inventive device when the tissue connection device according to the invention is used. This means that with the invention which is described here it is possible to perform for the first time in one single working step the resection of a section of the intestines with the simultaneous restoration of intestinal continuity. Furthermore, only the use of the suture clip device according to the invention as described herein makes an individual determination of the length of the intussusception possible while when using devices of the state of the art the length is more or less constant and/or accidental.

By using the tissue connection device according to the invention, the two halves of the intestine may, simultaneously with the removal of the tissue by one cut only, be connected with each other by means of clips. Thereby the time of the surgical intervention is shortened and the tissue is subjected to strain only once.

Advantageously, the head part and the counter-pressure plate holding device are guided by a guide member which is coupled to the head part and is guided in a linear direction in the counter-pressure plate holding device. The counter-pressure plate holding device is protected against twisting and is slidably supported on the guide member so that a precise orientation of the counter-pressure plate relative to the head part and/or relative to the connection member which is arranged in the head part is ensured.

Usually, the connection members are clips which penetrate the tissue with their ends to and can thereafter be bent in such a manner that they can adopt the shape of a B. In this way, the connection members clamp the two halves of the intestine with each other.

The dimensions of the clips before the connection is made and in the bent state, i.e. is in the connecting state can be in conformity with the conventional clip sizes.

Furthermore, it is advantageously provided that the counter-pressure plate holding device can be positioned in respect of the head part by means of an adjusting device. In this way, a defined distance between the head part and the counter-pressure plate can be adjusted in order to provide sufficient space for manipulation for the preparation of the tissue connection and in order to be able to adjust for the tissue connection the required minimal distance between the head part and the counter-pressure plate for clamping tissue between the head part and the counter-pressure plate.

Preferably a spindle drive is to be used as adjusting means, with the thread of the spindle being arranged at the guide member and a clasp nut that co-operates with the spindle that can be turned and is arranged at the counter-pressure plate holding device by means of an engagement ring that functions as a carrier so that the distance between the counter-pressure plate holding device and the head part can be adjusted and set. This means that the guide member is provided on one section of its outer wall with a thread so that the guide member itself forms the spindle. The clasp nut which is operatively connected with the spindle causes, when being turned, a linear forward movement of the counter-pressure plate holding device along the longitudinal axis of the guide member since the clasp nut is engaged by the engagement ring that is arranged on the counter-pressure plate holding device.

Advantageously, a plurality of connection members can be housed in the reception device within the head part with the connection members being clips which are held in a ring-shaped magazine and can be bent.

Alternatively, only one connection member can, however, also be used. When a plurality of connection members is used it is of advantage that the magazine is designed to in such a way that it can be re-loaded for the purpose of a repeated use. This feature of re-loadability of the magazine makes it possible to use the inventive tissue connection device several times. For the deformation of the clips which strike contact with the counter-pressure plates when the inventive tissue connection device is actuated, the counter-pressure plate is provided with groove-shaped indentations which cause that the clip ends are guided in the direction of the counter-pressure plate when they are de-formed by the pressure that is applied onto the clips. By virtue of the anti-twist means of the counter-pressure plate holding device relative to the guide member it is ensured that in each case a groove-shaped indentation in the counter-pressure plate is arranged opposite a clip that is housed within the magazine.

Furthermore, it is provided that a pull rod is arranged in the guide member which is located at its head side end with a punch which is located in its head part for moving the connection members in the direction of the counter-pressure plate and which is coupled at the opposite end to an actuation means for applying a tensile force onto the pull rod. This punch acts as a piston and is provided with a punch plate which is connected with the pull rod via plate supports. Alternatively, the punch plate may also be connected with the pull rod by means of a supporting ring-shaped connection.

For ensuring a comfortable manual operability of the actuation means, the same is designed according to the principle of an inverted toggle press. This means that the levers of the toggle press are flexibly coupled by means of joints to the guide member via manually operable actuation members. Consequently, when the actuation members are pressed against each other, the levers can be shifted in such a manner that, due to their hinged arrangement at the guide member and the coupling to the pull rod, they can easily shift the said pull rod. Through the movement of the pull rod, the punch which is arranged on the head side end of the pull rod is pulled in the direction of the handle side end of the tissue connection device so that the connection members abutting the punch are pressed through the tissue that is to be connected onto the counter-pressure plate where they are deformed.

For the removal of invaginations, such as for instance prolapses, as well as for the resection of pathological changes, such as for instance haemorrhoids, the inventive to connection device is provided with a cutting means in the form of a ring-shaped knife within the ring-shaped magazine which can also be moved by the punch at the pull rod in the direction of the counter-pressure plate. Excess tissue is removed by using the knife. In order to use the tissue connection device according to the invention also for the formation of nipple valves, it is provided that the ring-shaped knife can either be dismounted or deactivated in order to perform only a clamping operation and no cutting operation when the tissue connection device is employed. According to the invention, the knife is arranged—just as the connection members—within the head part thereby also ensuring a free accessibility of the tissue which is located behind the counter-pressure plate and between the columns.

Since the head part and the counter-pressure plate perform a relative movement when the distance between them is adjusted, it is provided that spacers are arranged on the guide member which facilitate the said relative movement between the counter-pressure plate holding device, on the one hand, and the guide member and the head part, on the other hand, without any jamming. An anti-twist means of the counter-pressure plate holding device can be accomplished by a shoulder or a lug which project from the counter-pressure plate holding device between the spacers. In this manner, it is positively ensured that no relative twisting takes place between the guide member and the counter-pressure plate holding device.

Furthermore, it is preferably provided that the counter-pressure plate holding device is equipped with a plurality of columns which are arranged at the outer circumference of the counter-pressure plate and extend therefrom in the direction of the handle side end up to an area of the taper of the counter-pressure plate holding device.

The area of taper, too, can be formed by the columns. In an alternative embodiment, the columns end at an internal taper segment of the counter-pressure plate holding device that forms the said taper. In the latter alternative, the counter-pressure plate holding device is provided in the internal taper segment with openings for the passage of the sutures and for facilitating the view into the site of the operation. The part of the counter-pressure plate holding device which follows the taper has an essentially hollow cylindrical shape in the direction of the handle side end with the internal diameter of the hollow cylindrical segment corresponding to the radial maximal distance of the spacers on the guide member to each other. This ensures a clearance-minimised or clearance-free guidance of the counter-pressure plate holding device on the guide member.

With a view to facilitating the surgical intervention, it is moreover provided that the hollow cylindrical part of the counter-pressure plate holding device has suture thread fixation means at its outer surface. The threads of a preparatory suture, for instance those of a purse-string suture for tissue fixation and tissue positioning can be laid at these suture thread fixation means. In this context, the suture thread fixation means are preferably designed in such a way that they can hold the preparatory threads onto which a constant tensile strength is applied. In a preferred configuration it is provided that at least some of the suture thread fixation means are so-called Curry cleats, which are known from sailing sports.

Such Curry clips make it possible to fix the threads within the shortest possible period of time with minimal efforts for their fixing. As an alternative to these Curry clips, other suture thread clips may also be used by means of which also threads can be fixed which are not subjected to a constant tensile strength. Simple small hooks may, for instance, be used to which threads can be tied.

Furthermore, an advantage of the invention is that the head part can be divided for the purpose of the assembly and the reception of the punch. Here, it may be provided that a cone-shaped end of the head part is detachably connected with the cylindrical segment of the head part. After detaching the cone-shaped end, the pull rod of the punch may be pushed into the guide member through an opening in the head part and through the same until the punch reaches the magazine and/or ends with the space that is provided for the reception of the magazine. Thereafter the cone-shaped end can again be firmly arranged at the cylindrical segment of the head part. The connection of the cylindrical segment with the guide member can for instance be accomplished by means of minimally thin radial bars which are arranged in recesses in the magazine or also via a spacer which is arranged centrally on the axis of the guide part and the pull rod. As an alternative to that, it may also be provided that a cone-shaped segment follows the head side end of the punch which facilitates the insertion of the device into the organ that is to undergo surgery. In this embodiment, the head part is open towards the head side end and ends at the cone-shaped segment at the end of the punch.

In order to guarantee at least for some components and/or sub-assemblies of the tissue connection device according to the invention a repeated use, it may be provided that the head part, the punch and the counter-pressure plate can be exchanged so that one and the same basic configuration of the tissue connection device can be combined with head parts, punches and counter-pressure plates of different sizes. It will be appreciated that the sizes of the mentioned components which are to be combined are compatible with each other. For different purposes, different diameters of the mentioned components may be used so that in each case two circular sutures which are created by clips can be laid with the following diameters:

a) 21 mm and 25 mm for the nipple valve stabilisation in continent ileorespective urostomies,
b) 28 mm and 31 mm as standard device for the anal and haemorrhoidal prolapse,
c) 34 mm and 38 mm for tubular rectum resections.

The exchangeability of the components that are to be exchanged can be advantageously accomplished through screw couplings and/or plug-and-socket connections.

When the tissue connection devices according to the invention are employed as one-way devices in accordance with the stated indications, the devices are to be equipped with different diameters of the head and/or of the magazine as indicated under a), b) and c).

Summarising, the essential advantage of the invention is that the invaginated section of the intestine need not be pulled into a housing with a limited capacity, but is at first put over the guide member of the device. The clip magazine and the cutting means are arranged in the head part of the device at the end of the guide member. For compressing the intestinal collars that are to be connected and as a counter-pressure plate for bending the clips, a relevant ring is pushed over the outside of the intussusception. Here, the adjusting means is designed in such a way that the intussusception remains to the largest possible extent freely accessible. In surgery in the vicinity of the anus (anal and rectum prolapse as well as internal prolapse) the anus is kept is open by means of a ring speculum, in surgery at the open abdomen (nipple valves and nipple valve anastomoses) a speculum is not required.

The invention will now be described by way of example with reference to the accompanying drawings in which.

Figure 1:
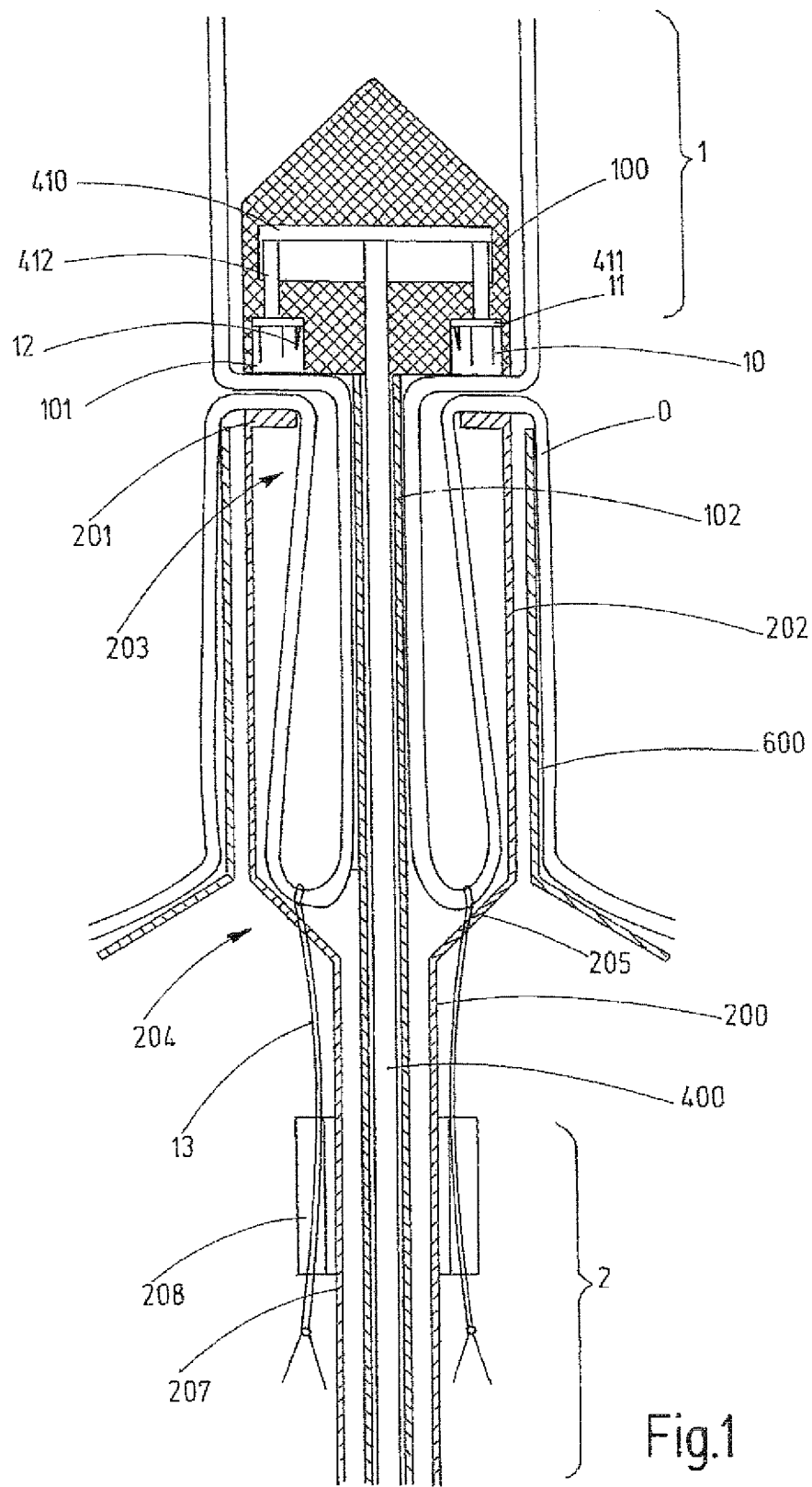
FIG. 1 is a sectional view of a head side end of an employed tissue connection device according to the invention.

The use of the tissue connection device according to the invention is shown in FIG. 1. As can be seen, the tissue 0, here depicted in the form of a thin tube, has already been pulled into the inventive tissue connection device and has been fixed there by is means of suture threads 13. In FIG. 1, only the head side part of the connection device is shown in order to make details in this area more easily recognisable. The tissue connection device according to the invention consists in this area of the head part 100 which is arranged at the head side end 1. Oriented towards the handle side end 2 is the counter-pressure plate holding device 200. When in use, the tissue connection device with its head part 100 has been guided through a ring speculum 600 which keeps the intestine end open at the head part 100 is now located behind the tissue area that is to removed by means of surgery. By means of suture threads 13 which were laid prior to the insertion of the tissue connection device, the tissue that is grasped by sutures can be pulled in the direction of the handle side end 2. Invaginations of the tissue 0 are pulled over the counter-pressure plate 201 which is arranged on the counter-pressure plate holding device 200 between the columns 202 which support the counter-pressure plate 201 and/or the counter-pressure plate 201 is pushed over the invagination. For arresting the tissue 0 which is to be removed the suture threads 13 are placed in suture fixation means 208. Along the longitudinal axis of the counter-pressure plate holding device 200 the guide member 102 is located in the same which is connected with the head part 100 at its head side end 1. The head part 100 is provided with a reception means 101 for receiving connection members 10 which are shown here as clips and for receiving a ring-shaped knife 12. The connection members 10 which are provided in the form of clips are housed in a magazine 11. Guided within the guide member 102 is the pull rod 400 of a punch 410 which is also arranged in the head part 100. The punch 410 is connected with a ring-shaped punch plate 411 via plate supports 412. The punch plate 411 sits in a neutral state close to the connection members 10 and/or to the magazine 11 which receives the connection members 10. When the head part 100 is arranged so close to the counter-pressure plate 201 that the tissue 0 which is located between the two components is slightly compressed, the pull rod 400 is pulled in the direction of the handle side end 2 so that the punch plate 411 which is connected with the pull rod 400 to via the plate supports 412 moves the magazine 11 and/or the connection members 10 which are housed in the magazine 11 in the direction of the counter-pressure plate 201. This is done until the ends of the connection members which are provided as clips rest on the counter-pressure plate 201 and get deformed due to further forces so that the tissue 0 which is located between the head part 100 and the is counter-pressure plate 201 is clamped together by the connection members 10. Simultaneously with the forward movement of the connection members, the ring-shaped knife 12 is moved by means of the punch plate 411 in the direction of the counter-pressure plate 201 so that the tissue 0 which is connected with each other is severed in the internal diameter of the ring-shaped suture that has been created. In this manner, with one movement of the pull rod 400, sections of the intestines may be connected and excess tissue 0 at the sections of the intestines may be sheared off simultaneously. In this manner, a prolapse which corresponds to the tissue 0 which is to be removed may be removed easily and quickly. In addition to that, haemorrhoids may be resected by pulling sections of the intestine from the direction of the intestinal exit behind the haemorrhoids by means of preparatory sutures into the tissue connection device, followed by the described clamping and suturing operations. Owing to the shortening of the tissue within the intestine, the haemorrhoids are pulled into the intestine (haemorrhoid fixation).

When the ring-shaped knife 12 is deactivated and/or is not attached, nipples for valve formation within the intestine may be easily created in the described manner by means of the adjustment of the tissue 0 in the space 203 that is located behind the pressure plate followed by the clamping of the tissue.

It is obvious that a great amount of tissue 0 which is to be treated and/or which is to be removed may be pulled behind the counter-pressure plate 201 into the space 203 that is located there between the columns 202. This is made possible by the fact that the connection members 10 for performing the tissue connection as well as the magazine 11 which receives the connection members 10 and the ring-shaped knife 12 are completely arranged within the head part 100 of the inventive tissue connection device. Consequently, the space 203 behind the counter-pressure plate 201 is completely available for the reception of the tissue 0. By providing the counter-pressure plate holding device 200 with columns 202, it is possible for the surgeon to intervene and/or to look, radially to the circumference of the counter-pressure plate holding device 200 and/or of the counter-pressure plate 201, into the space 203 behind the counter-pressure plate 201. This is also made possible by the arrangement of the columns 202 in the longitudinal direction of the tissue connection device. In this is manner it is possible to resect far more tissue with one cut than had been possible with conventional suture clip devices. This means that for large-size prolapses the use of only one suture clip device according to the invention is required instead of using—as has been the case so far—several one-way suture clip devices. Furthermore, the free accessibility of the space 203 behind the counter-pressure plate 201 makes the manual performance of the surgical intervention essentially easier for the surgeon and, above all, the size of the prolapse may be individually adjusted.

Figure 2:
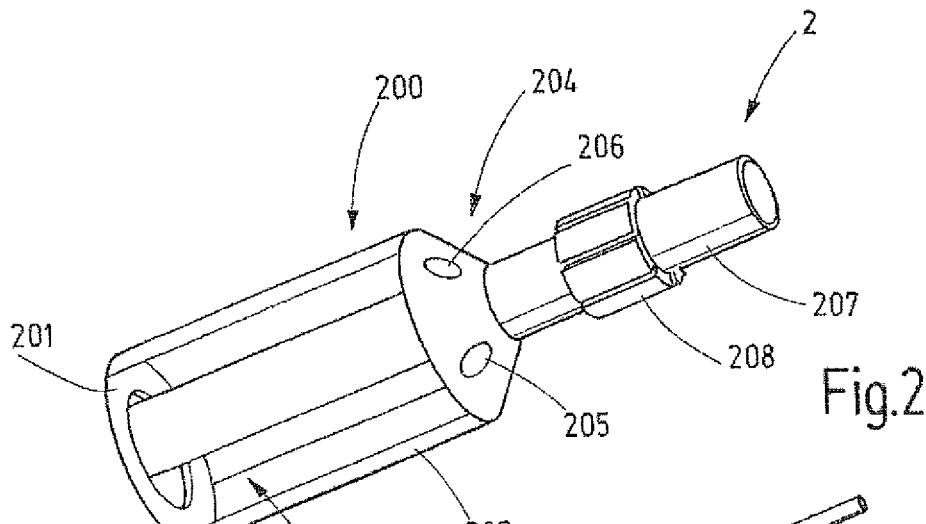
FIG. 2 is a perspective view of a counter-pressure plate holding device.

FIG. 2 shows a perspective view of the counter-pressure plate 200 holding device. The ring-shaped counter-pressure plate 201 is arranged at its head side end 1. The same is connected by four columns 202 which are provided in this embodiment with an area of the taper 204 of the counter-pressure plate holding device 200 which is in the present case designed as an internal taper segment 205. The internal taper segment 205 is provided with openings 206 for the passage of sutures 13 as well as for facilitating manual intervention and optical monitoring. The area of taper 204 is followed by a hollow cylindrical part 207. Suture fixation means 208 are radially arranged on the hollow cylindrical part 207.

Figure 3:
FIG. 3 is a perspective view of a punch.
Figure 4:
FIG. 4 is a perspective view of a head part with a guide member arranged on it.

FIG. 3 shows a perspective view of the punch 410 with the pull rod 400. Here, the pull rod 400 is arranged centrally within the punch 410. Plate supports 412 at the ends of which the punch plate 411 is supported are provided at the punch 410 and are aligned axially to the pull rod 400. As is shown in FIG. 1, the pull rod 400 is provided in a mounted state within the guide member 102 which is—as is shown in FIG. 4—firmly connected with the head part 100. The head part 100 with guide member 102 which is shown as a perspective view in FIG. 4 has a reception means 101 which is designed as a recess and faces the handle side end 2. When the punch 410 and the pull rod 400 are received in the head part 100 and/or in the guide member 102, the punch plate 411 may shift within the reception means 101.

Figure 5:
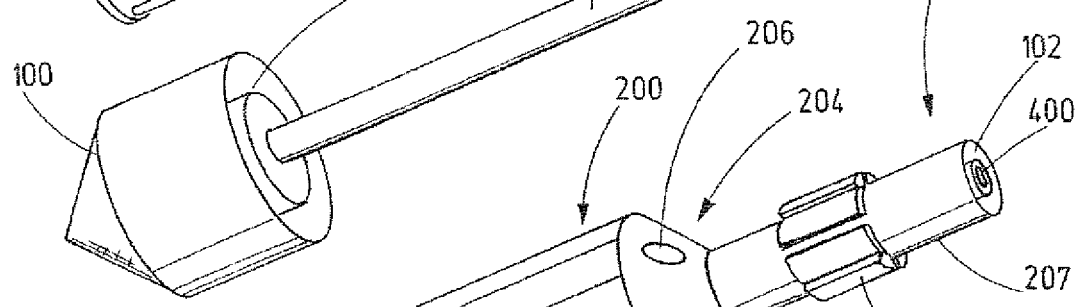
FIG. 5 is a perspective view of the head side end of the tissue connection device according to the invention.
Figure 5:
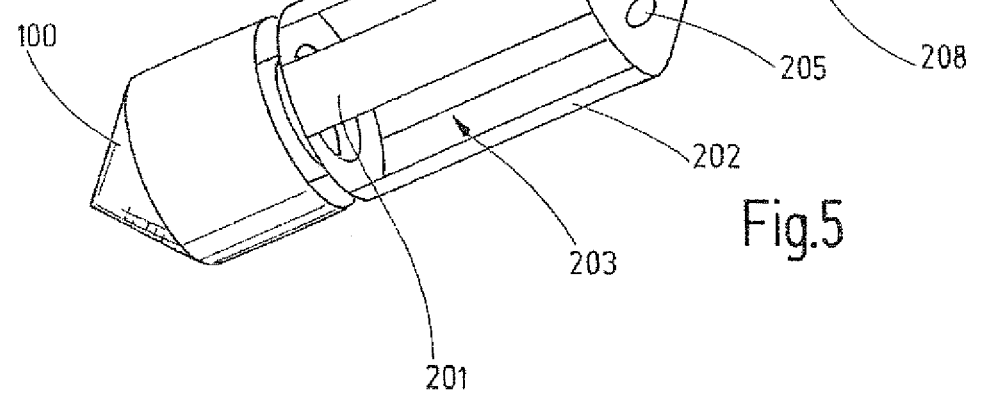

FIG. 5 shows in a perspective view and in a mounted state the components which are depicted in FIG. 2 to FIG. 4. At the handle side end 2 it can be seen that the guide member 102 is arranged within the hollow cylindrical part 207 of the counter-pressure plate holding device 200 and within the same the pull rod 400.

Figure 6:
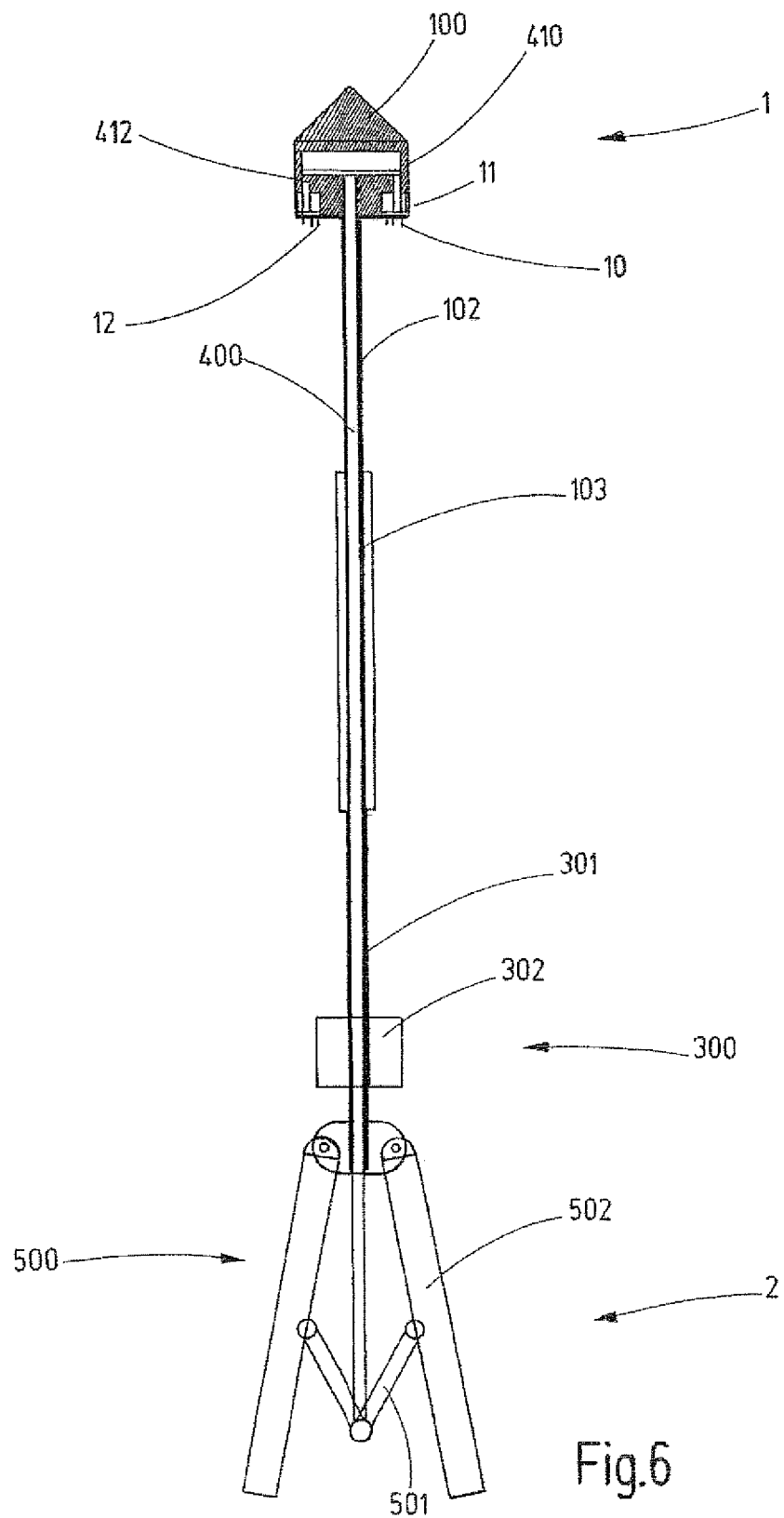
FIG. 6 is a side sectional view of a tissue connection device according to the invention without the counter-pressure plate holding device.

FIG. 6 is a diagrammatic representation of the inventive tissue connection device as a side elevation which for the purpose of illustrating the function does not contain a counter-pressure plate holding device.

This representation shows in particular the adjustment means 300 and the actuation means 500 for activating the tissue connection device. In order to ensure a correct guidance of the counter-pressure plate holding device (not shown) on the guide member 102, the same is provided at its outer surface with a spacer 103 arranged at a section of the same which co-operates as a guidance with the inner wall of the hollow cylindrical part 207 of the counter-pressure plate holding device 200. On another section of the guide member 102 external threads are provided whereby the guide member 102 forms a spindle 301. A clasp nut 302 which co-operates with the spindle thread is provided on the spindle 301. The spindle 301 and the clasp nut 302 form on the counter-pressure plate holding device 200, together with an engagement ring (not shown), the adjustment means for adjusting the distance between the counter-pressure plate holding device 200 and/or the counter-pressure plate 201 in respect of the head part 100. At the handle side end 2 of the tissue connection device the pull rod 400 projects from the guide member 102 and is flexibly connected with two levers 501 which are flexibly connected with their opposite ends with actuation members 502. When the actuation members 502 are actuated, the levers 501 are moved in accordance with the inverted principle of a toggle press in such a manner that the pull rod 400 is pulled out of the guide member 102 in the direction of the handle side end 2 so that the punch 411 in the head part 100 is also pulled in the direction of the handle side end 2 so that the connection members 10 are pushed out of the head part 100.

Figure 7:
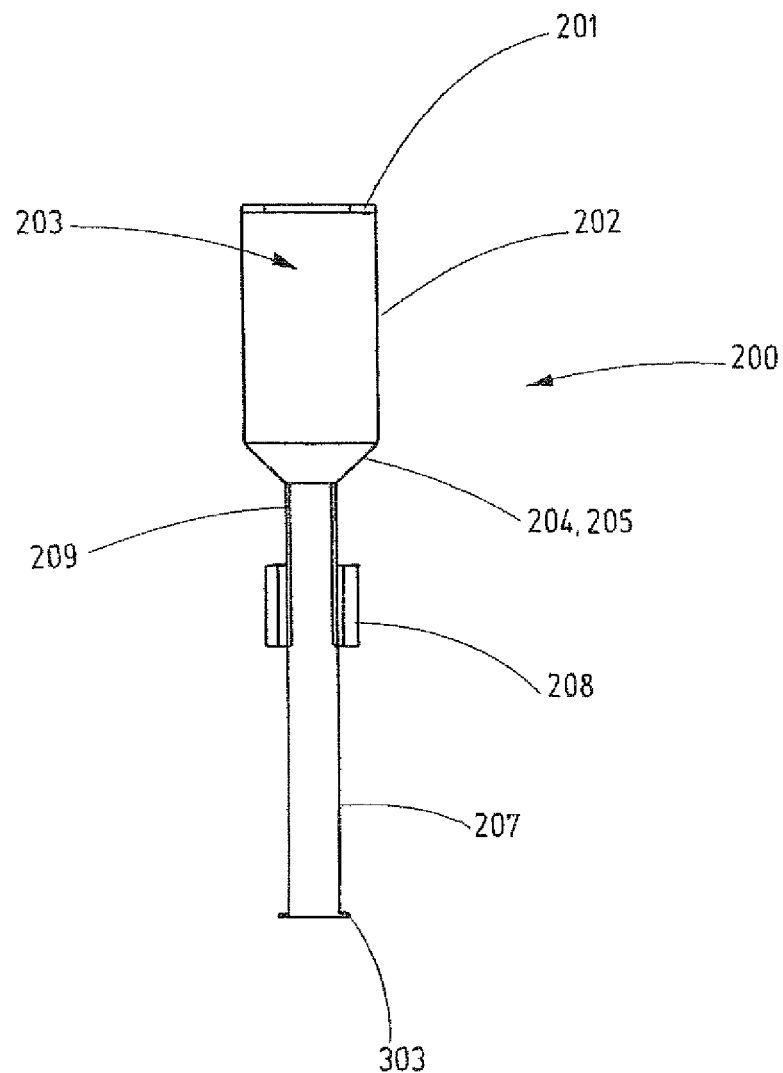
FIG. 7 is a side view of the counter-pressure plate holding device.

FIG. 7 shows in a side elevation the counter-pressure plate holding device 200 alone. FIG. 7 shows in particular the arrangement of the engagement ring 303 which is housed in the clasp nut 302 that is shown in FIG. 2. Furthermore, the anti-twist means 209 which is arranged within the hollow cylindrical part 207 is depicted which advantageously engages a gap between members of the spacer 103 on the guide element 102 thus making impossible a relative turning of the counter-pressure plate holding device 200 in respect of the guide member 102 and thus in respect of the head part 100 and the connection members 10 arranged within the same.

Figure 8:
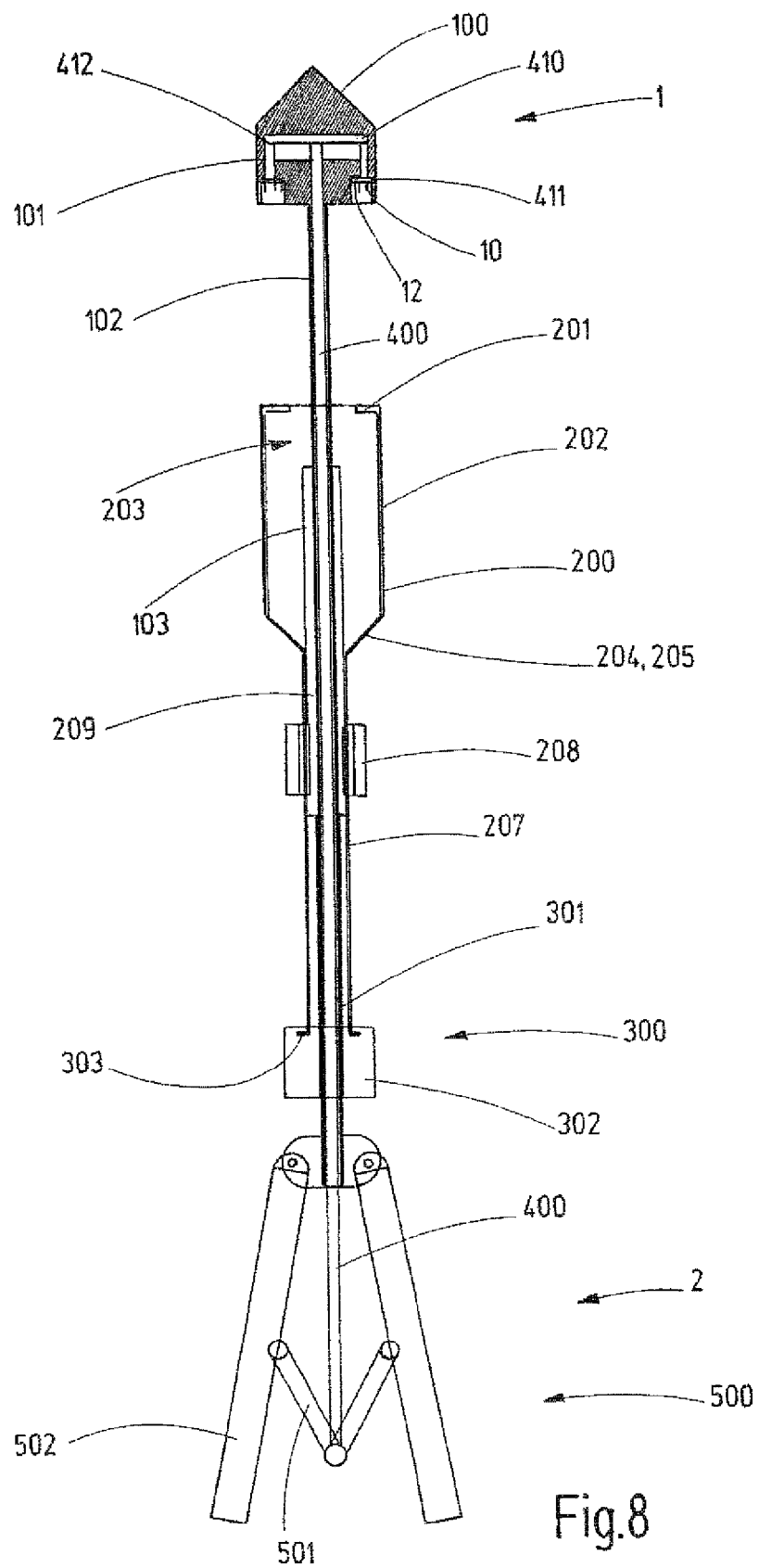
FIG. 8 is a side sectional view of the tissue connection device according to the invention in an open state and FIG. 9 is a side sectional view of the tissue connection device according to the to invention in a closed state.

FIG. 8 shows the tissue connection device according to the invention as a side elevation. It depicts the connection device in an open state, i.e. the head part 100 has a great distance to the counter-pressure plate 201. This state is used in particular when the connection device is introduced into the intestine and/or when the tissue 0 that is to be treated is prepared for tissue connection. In this state, the clasp nut 302 is located at the handle side end of the spindle 301. When the clasp nut 302 is turned, the same shifts along the longitudinal axis of the guide member 102 and takes, due to the arrangement of the engagement ring 303 at the end of the counter-pressure plate holding device 200, the same along in the direction of the head part 100. In this manner, the distance between the counter-pressure plate 201 and the head part 100 can be adjusted by turning the clasp nut 302.

Figure 9:
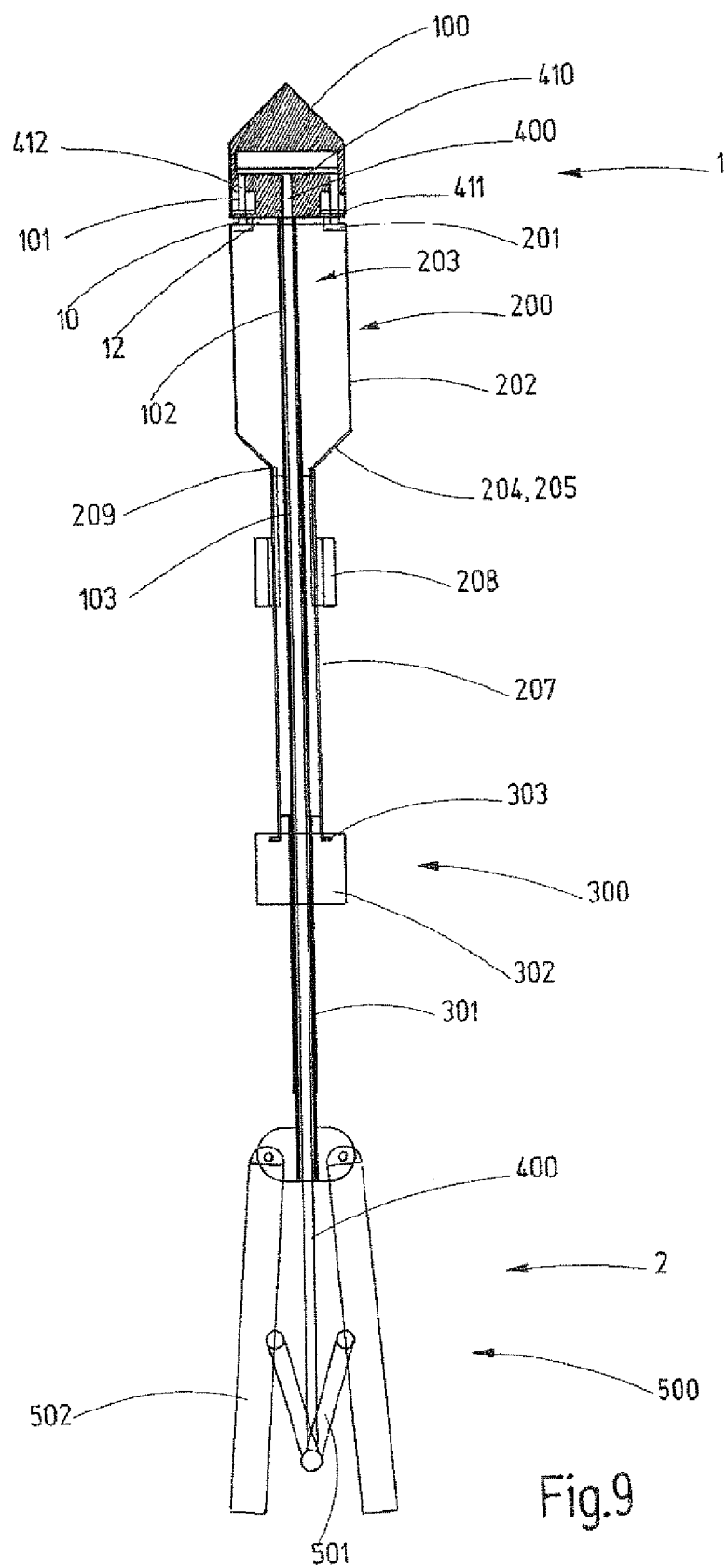

FIG. 9 shows the inventive tissue connection device in a closed and actuated state. For closing the connection device, the clasp nut 302 on the spindle 301 was turned in such a manner that, while taking along the engagement ring 303 and thus the entire counter-pressure plate holding device 200, it has moved up to a minimal distance from the head part 100. This position of the counter-pressure plate holding device 200 in respect of the head part 100 is in conformity with the state of the connection device as depicted in FIG. 1 where the connection device clamps between the counter-pressure plate 201 and the head part 100 the tissue 0 that is to be removed and/or to be clamped. By pressing together the actuation members 502, the levers 501 have been moved in such a way that they have partly pulled the pull rod 400 out of the guide member 102 so that, on the other hand, the punch 410 that is arranged on the pull rod 400 has shifted in the direction of the counter-pressure plate 201. It can be seen that by means of the shifting of the punch 410 the connection elements 10 as well as the ring-shaped knife 12 have moved out of the head part 100 to such an extent that they rest against the counter-pressure plate 201. When more tensile strength is applied on the pull rod 400, the connection members 10 are deformed on the counter-pressure plate 201 in such a manner that a clamping connection of the is two tissue halves is achieved.

At the same time, the ring-shaped knife 12 separates within the internal area of the laid circular sutures the tissue in such a manner that a free passage within the created tissue jacket is achieved. By simply releasing the actuation means 502 and/or by moving them away from each other, the pull rod can be moved back one again in the direction of the head part 100 so that the ring-shaped knife 12 is again arranged within the reception means 101 of the head part 100. By turning back the clasp nut 302 on the spindle 301, an opening of the connection device can be created to enable the removal of the tissue connection device from the site of the operation.

LIST OF REFERENCE NUMERALS

0 Tissue
1 Head side end
2 Handle side end
10 Connection member
11 Magazine
12 Ring-shaped knife
13 Suture thread
100 Head part
101 Reception means
102 Guide member
103 Spacer
200 Counter-pressure plate holding device
201 Counter-pressure plate
202 Column
203 Space behind the counter-pressure plate
204 Area of the taper of the counter-pressure plate holding device
205 Internal taper segment
206 Opening
207 Hollow cylindrical part
208 Thread fixation means
209 Anti-twist means
300 Adjustment means
301 Spindle
302 Clasp nut
303 Engagement ring
400 Pull rod
410 Punch
411 Punch plate
412 Plate supports
500 Actuation means
501 Lever
502 Actuation member
600 Ring speculum

The invention claimed is:

1. An anastomotic tissue connection device in the form of a circular suture clip device which has a head side end and a handle side end, with a head part arranged at the head side end comprising a reception means for receiving at least one connection member for the connection of the tissue and which, furthermore, is provided with a counter-pressure plate being firmly arranged at a counter-pressure plate holding device and facing the head part for retention during the introduction of the connection member into the tissue that is to be connected, with the head part and the counter-pressure plate holding device being relatively movable towards each other, wherein the counter-pressure plate is arranged between the reception means and the handle side end, and wherein, for a support of the counter-pressure plate, the counter-pressure plate holding device forms a plurality of columns which are arranged at an outer circumference of the counter-pressure plate and extend therefrom in a direction of the handle side end and which are positioned and dimensioned in a thin design in such a manner that space directly behind the counter-pressure plate is either a circumferentially open space or a circumferentially closed space, the circumferentially closed space being confined by the plurality of columns and the circumferentially open space being unconfined by the plurality of columns such that the circumferentially open space is freely accessible radially to the outer circumference of the counter-pressure plate.

2. The anastomotic tissue connection device according to claim 1, wherein the head part and the counter-pressure plate holding device are guided by a guide member which is coupled to the head part and which is guided in a linear direction in the counter-pressure plate holding device.

3. The anastomotic tissue connection device according claim 2, wherein the counter-pressure plate holding device can be positioned by means of an adjusting means with respect to the head part.

4. The anastomotic tissue connection device according to claim 3, wherein the adjusting means is a spindle drive with a thread of a spindle of the spindle drive being arranged at the guide member and that a clasp nut that co-operates with the spindle can be turned and is arranged at the counter-pressure plate holding device by means of an engagement ring that functions as a carrier so that a distance between the counter-pressure plate holding device and the head part can be adjusted and set.

5. The anastomotic tissue connection device according to claim 2, wherein one connection member or a plurality of connection members can be received in a receiving means in the head part.

6. The anastomotic tissue connection device according to claim 5, wherein a ring-shaped knife is arranged within the ring-shaped magazine which can also be moved in a direction of the counter-pressure plate by means of a punch at a pull rod.

7. The anastomotic tissue connection device according to claim 2, wherein a pull rod is arranged in the guide member which is provided at its head side end with a punch which is located in the head part for moving the connection members in a direction of the counter-pressure plate and which is coupled at the opposite end to an actuation means for applying a tensile force onto the pull rod.

8. The anastomotic tissue connection device according to claim 7, wherein the actuation means functions according to the principle of an inverted toggle press.

9. The anastomotic tissue connection device according to claim 8, wherein levers of the inverted toggle press are coupled by means of joints to the guide member via manually operable actuation members.

10. The anastomotic tissue connection device according to claim 7, wherein the head part can be divided for the purpose of the assembly and reception of the punch.

11. The anastomotic tissue connection device according to claim 7, wherein the head part, the punch and the counter-pressure plate are exchangeable so that the same basic configuration of the tissue connection device can be combined with head parts, punches and counter-pressure plates of different sizes.

12. The anastomotic tissue connection device according to claim 2, wherein spacers are arranged on the guide member which facilitate a relative shifting between the counter-pressure plate holding device, on the one hand, and the guide member and the head part, on the other hand, without getting jammed.

13. The anastomotic tissue connection device according to claim 12, wherein a part of the counter-pressure plate holding device which follows a tapering has an essentially hollow cylindrical shape wherein an internal diameter of the hollow cylindrical part corresponds to a radial maximal distance of the spacers.

14. The anastomotic tissue connection device according to claim 13, wherein the hollow cylindrical part of the counter-pressure plate holding device is provided at its outer circumference with suture thread fixing means.

15. The anastomotic tissue connection device according to claim 14, wherein the thread fixing means are Curry cleats.

16. The anastomotic tissue connection device according to claim 2, wherein the plurality of columns extend up to an area of a tapering of the counter-pressure plate holding device.

17. The anastomotic tissue connection device according to claim 1, wherein the circumferentially open space directly behind the counter-pressure plate, that is freely accessible, extends away from the handle side end directly to the counter-pressure plate.

18. The anastomotic tissue connection device according to claim 1, wherein the counter-pressure plate is positioned on the plurality of column between the reception means and the handle side end.

* * * * *